(12) United States Patent
Cody

(10) Patent No.: US 6,902,938 B1
(45) Date of Patent: Jun. 7, 2005

(54) CHEMICAL ANALYSIS METHOD FOR MULTIPLEXED SAMPLES

(75) Inventor: Robert B. Cody, Portsmouth, NH (US)

(73) Assignee: Jeol USA, Inc., Peabody, MA (US)

( * ) Notice: Subject to any disclaimer, the term of this patent is extended or adjusted under 35 U.S.C. 154(b) by 537 days.

(21) Appl. No.: 09/685,297

(22) Filed: Oct. 10, 2000

(51) Int. Cl.[7] .............................. G01N 1/00; G01N 1/10; G01N 1/22; G01N 33/00; H01J 49/00
(52) U.S. Cl. ...................... 436/174; 436/173; 436/180; 436/181; 436/179; 250/281; 250/282; 250/288
(58) Field of Search ................................. 436/180, 173, 436/174, 179, 181; 250/281, 282, 288

(56) References Cited

U.S. PATENT DOCUMENTS

| | | | | |
|---|---|---|---|---|
| 3,600,953 A | * | 8/1971 | Israeli | 73/423 A |
| 3,759,667 A | * | 9/1973 | Bannister et al. | 422/81 |
| 3,909,136 A | * | 9/1975 | Thomas | 356/181 |
| 3,929,413 A | * | 12/1975 | Young et al. | 23/259 |
| 4,130,394 A | * | 12/1978 | Negersmith | 23/230 R |
| 4,253,846 A | * | 3/1981 | Smythe et al. | 23/230 R |
| 4,259,291 A | * | 3/1981 | Smythe | 422/82 |
| 4,328,185 A | * | 5/1982 | Reasons et al. | 422/82 |
| 4,517,302 A | * | 5/1985 | Saros | 436/180 |
| 4,708,782 A | * | 11/1987 | Andresen et al. | |
| 4,931,639 A | * | 6/1990 | McLafferty | |
| 4,975,576 A | * | 12/1990 | Federer et al. | |
| 4,978,852 A | * | 12/1990 | Williams et al. | |
| 5,268,147 A | * | 12/1993 | Zabetakis et al. | 422/82 |
| 5,399,497 A | * | 3/1995 | Kumar et al. | 436/53 |
| 5,466,946 A | * | 11/1995 | Kleinschmitt et al. | 250/577 |
| 5,498,545 A | * | 3/1996 | Vestal | |
| 5,508,204 A | * | 4/1996 | Norman | |
| 5,538,897 A | * | 7/1996 | Yates, III et al. | |
| 6,066,848 A | * | 5/2000 | Kassel et al. | |
| 6,150,119 A | * | 11/2000 | Kopf-Sill et al. | 435/7.1 |

* cited by examiner

Primary Examiner—Jill Warden
Assistant Examiner—Brian R. Gordon
(74) Attorney, Agent, or Firm—The Webb Law Firm

(57) ABSTRACT

Analyzing a plurality of fluid specimens with a single analyzing instrument comprising introducing different combinations of specimens into a homogenizing volume to create a homogenized specimen and with a programmed digital computer mathematically processing the recorded results to produce analyses corresponding to individual fluid specimens.

8 Claims, 1 Drawing Sheet

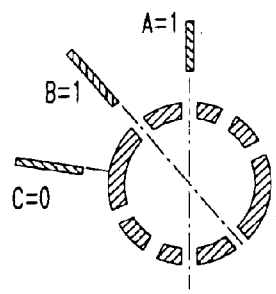 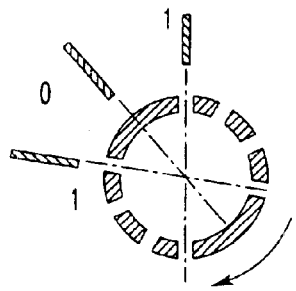 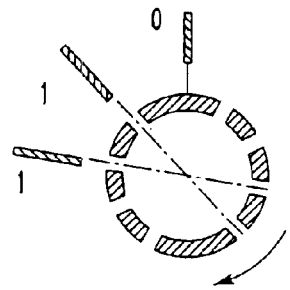
FIG.1(a)   FIG.1(b)   FIG.1(c)
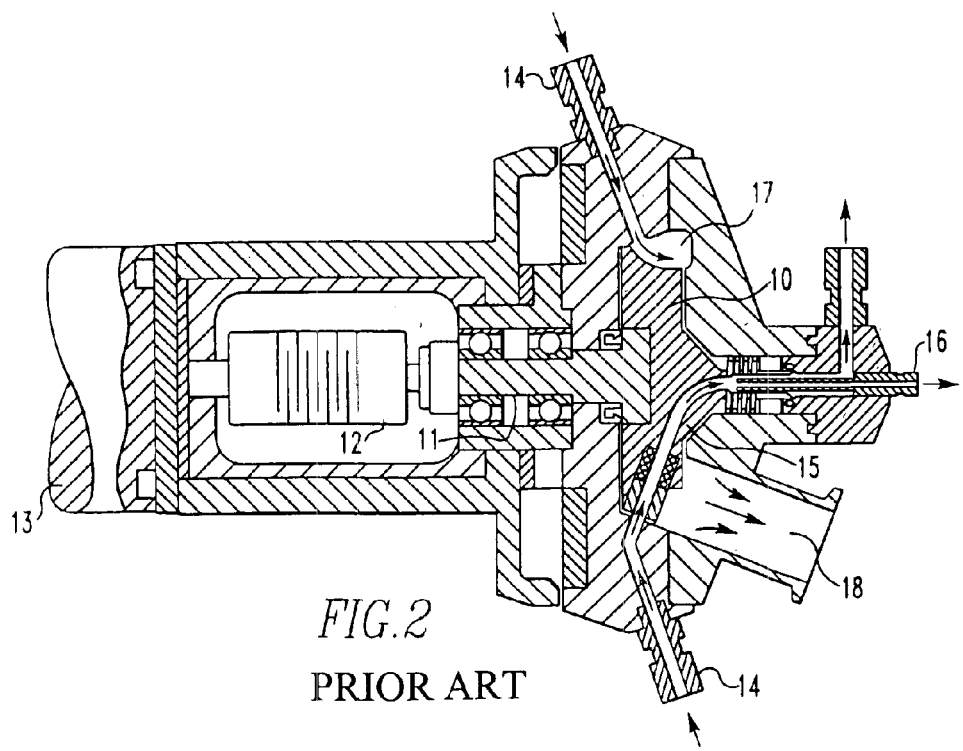
FIG.2
PRIOR ART

CHEMICAL ANALYSIS METHOD FOR MULTIPLEXED SAMPLES

FIELD OF THE INVENTION

This invention relates to analysis of large numbers of fluid specimens in instruments, such as mass spectrometers with a single instrument.

BACKGROUND OF THE INVENTION

One prior method of analyzing large numbers of specimens with a single instrument is with a multiplexed sampling system wherein samples are prepared and supplied to the instrument one at a time. For example, several electrospray needles and a rotating barrier with a hole that allows sprayed fluid streams emerging from the needles to be sampled one at a time has been proposed. Another approach is to provide a gas sampler that sequentially diverts one of a plurality of gas streams to an instrument. One commercially available selector valve performs rapid sample switching between up to 40 sample streams. The problem with either of these multiplexed sampling approaches is that only one specimen is analyzed at a time. To improve the signal-to-noise ratio of the results of the analysis, it is necessary to repeat each sample over and over again.

According to this invention, Hadamard transform or another transform technique is used to analyze multiple specimens simultaneously. This improves the signal-to-noise ratio by a factor of:

$$\frac{(N+1)/2}{N^{1/2}}$$

for N separate specimens over the same measurement time or it would reduce the time 4/N to obtain the same signal-to-noise ratio as the individual measurement approach.

The Hadamard transform method is well known in spectroscopy and it is essentially based on solving n simultaneous equations in n unknowns to deconvolute the stored results. Hadamard transform methods have been used in MS/MS experiments in a Fourier transform mass spectrometer as explained by Loh, Williams, McLafferty and Cody in "Simultaneous MS-II Measurements Using Hadamard Transform Fourier Transform Mass Spectrometry", *Analytical Chemistry* (1988). In that case, different combinations of precursor ions were selected for dissociation. From the resulting spectra, individual daughter spectra were obtained by solving simultaneous equations. The Hadamard transform method has also been applied to time-of-flight mass analyzers wherein multiple testing conditions are simultaneously used with the same specimen followed by deconvolution with Hadamard transforms as set forth in Franzen U.S. Pat. No. 5,719,392.

SUMMARY OF THE INVENTION

It is an advantage, according to this invention, to provide a multiplexed sampling method wherein a plurality of fluid samples are analyzed simultaneously to improve the signal-to-noise ratio for a given time period or to shorten the time period for a given signal-to-noise ratio.

Briefly, according to this invention, there is provided a method for analyzing a plurality of fluid specimens with a single analyzing instrument. It comprises the steps for:

a) preparing a plurality of N fluid specimens, b) introducing a first combination of r specimens wherein r is less than N into a homogenizing volume to create a homogenized specimen, c) introducing at least a portion of the homogenized specimen to the analyzing instrument and recording the results of the analysis maintaining an association with the combination of r specimens, d) introducing additional different combinations of specimens into said homogenizing volume and repeating steps b) and c), and e) with a programmed digital computer mathematically processing the recorded results to produce analyses corresponding to individual fluid specimens.

In one embodiment, the fluid specimens are gaseous specimens diluted with a carrier gas and the analyzing instrument is a mass spectrometer. The mathematical processing comprises deconvolution wherein the mathematical processing comprises a Hadamard transform.

According to a preferred method, each specimen is directed into the homogenizing volume from individual nozzles connected to electronically controlled valves. The nozzle sizes, pressure drops therethrough, and open times of the valves are controlled to introduce a specified mass of each fluid specimen into the homogenizing volume. Normally, when nozzles are not supplying fluid specimen to the homogenizing volume, the flow of the specimen is diverted and continued.

Preferably, the number of specimens N is an odd number greater than 2 and r is an even number equal to (N+1)/2.

BRIEF DESCRIPTION OF THE DRAWINGS

Further features and other objects and advantages will become clear from the following detailed description made with reference to the drawings in which:

FIGS. 1(a), 1(b), and 1(c) illustrate the use of a rotating mask to select groups of fluid samples; and FIG. 2 is a section view through a rotating selector for selecting groups of gas samples.

DESCRIPTION OF THE PREFERRED EMBODIMENTS

This invention has application to mass spectrometry, for example. A mass spectrometer produces ions from chemical substances that are to be analyzed. The mass spectrometer then uses electric and magnetic fields to measure the mass of the charged particles. The masses and the relative abundance of the ions in a mass spectrum can be used to determine the structure and composition of molecules. A magnetic sector analyzer (just one form of mass spectrometer) separates ions according to their momentum (the product of their mass times their velocity). An electric sector analyzer separates the ions according to their kinetic energy. Both magnetic sectors and electric sectors are used in the high resolution double-focusing mass spectrometers. In its simplest mode of operation of the double-focusing mass spectrometer, the ions are accelerated at a constant potential into the electric sector, the electric sector is maintained at a constant potential, and the strength of the magnetic sector is varied. As the field strength of the magnetic sector is swept, ions of different mass-to-charge ratios are brought to focus on a detector slit. The detector counts the ions passing through the slit and the count versus the field strength (which in turn correlates to mass-to-charge ratio) comprises the mass spectrum. In the simple case, ions from only one sample at a time are accelerated into the electric field. Mass spectra can be gathered using other types of mass spectrometers, for example, quadrupole mass spectrometers, time-of-flight mass spectrometers, quadrupole ion trap mass spectrometers, and Fourier transform mass spectrometers.

As with the double-focusing mass spectrometers, one sample at a time is tested.

As already explained, a chemical compound or fragment thereof must be ionized in order to be analyzed by mass spectrometry. Any number of ionization methods are used, for example, electron impact ionization, chemical ionization, field ionization, and fast atom bombardment, to mention just a few. In each case, the sample is passed into an ionization chamber and ions are drawn out of the chamber and accelerated into the mass spectrometer. According to this invention, more than one sample at a time is introduced into the ionization chamber. It is not necessary that each specimen have identical mass as each other specimen, but it is necessary that each time a specimen is introduced, the same mass is introduced. The combinations of samples to be passed into the ionization chamber are selected according to Hadamard techniques. The simplest case would be introduction of three samples, two at a time. In this case, three different mass spectrums would be gathered, none of which would be the spectrum of any one of the samples. The three spectrums are digitized and stored in a computer database. They can then be deconvoluted by mathematical techniques.

Several techniques are possible for physically combining fluid, and more particularly, gas samples prior to introduction into the ionization chamber. One implementation comprises using a plurality of electrospray needles and a rotating barrier with a mask having openings that pass a selected number of sprays at any given time to the center thereof where they can be mixed and channeled to the ionization chamber. FIGS. 1($a$), 1($b$), and 1($c$) schematically illustrate the rotating mask at three positions for the trivial case of three spays, one for each of three samples.

FIG. 2. schematically shows a diversion valve for selecting samples. This is a prior art valve that was originally designed to pass one sample at a time modified to pass multiple samples at one time. The rotor is provided with multiple sample inlet connections instead of only a single sample inlet connection. Referring to FIG. 2, a rotor 10 is driven by shaft 11 and drive coupling 12, and drive motor and encoder 13. The rotor is provided with a plurality of sample transfer passages 15 for diverting sample flow from sample inlets to the sampling probe 16. The non-selected sample flow exhausts to an exhaust annulus 17 that delivers the mixed non-selected samples to a waste exhaust 18.

Applied Bioanalytical has demonstrated a microchip device having sprays that can be switched on or off electronically, so a "mask" could be omitted and the spray combinations could be generated electronically.

Let a, b, and c represent the results of measuring spray channels A, B, and C independently, and let x, y, and z represent the results of the combined sprays in steps 1, 2, and 3, respectively in the three sample example. If we represent the example above in matrix notation, $$\begin{pmatrix} x \\ y \\ z \end{pmatrix} = \begin{pmatrix} 1 & 1 & 0 \\ 1 & 0 & 1 \\ 0 & 1 & 1 \end{pmatrix} \begin{pmatrix} a \\ b \\ c \end{pmatrix}$$

The original results can be obtained by using an inverse matrix:

$$\begin{pmatrix} a \\ b \\ c \end{pmatrix} = \begin{pmatrix} 1 & 1 & -1 \\ 1 & -1 & 1 \\ -1 & 1 & 1 \end{pmatrix} \begin{pmatrix} x \\ y \\ z \end{pmatrix}$$

The improvement in signal-to-noise in the three sprayer case is:

$$\frac{2}{\sqrt{3}} = 1.15$$

The improvement is greater for larger numbers of spray nozzles. For seven sprays, the improvement in signal-to-noise is:

$$\frac{4}{\sqrt{7}} = 1.51$$

for the sample measurement time as the individual measurements, or the same signal-to-noise ratio could be obtained in roughly half (½) the time.

Even numbers of sprays are not suitable for this method, so a 96-spray device would have to be modified to a 95-spray device. For a 95-spray device, the improvement in signal-to-noise would be:

$$\frac{48}{\sqrt{95}} = 4.9$$

or the same signal-to-noise ratio could be obtained in 4/95=0.04 the time required for individual measurements.

One can imagine extending this concept to other multiple sampling applications. One such example is matrix-assisted laser desorption ionization (MALDI). In MALDI, multiple samples are placed on plates with (for example) 96 sample spots per plate. Samples are typically measured one at a time by firing a laser at the spot and using a time-of-flight mass spectrometer to analyze the ions produced by laser desorption. It is common practice to average multiple laser shots per spot to get good signal-to-noise ratios. One can imagine firing multiple laser beams (or a split laser beam) at the sample spots in combinations defined by Hadamard transform principles and then solving for the spectra from each individual spot with the resulting gain in signal-to-noise ratios, or a reduction in analysis time.

The method described herein is applicable to other analytical methods wherein multiple fluid streams can be sampled and combined for analysis.

Having thus described my invention with the detail and particularity required by the Patent Laws, what is desired protected by Letters Patent is set forth in the following claims.

1. A method for analyzing a plurality of fluid specimens consisting essentially of compounds and fragments thereof with a single analyzing instrument wherein multiple fluid streams can be sampled and combined comprising the steps for:
   a) preparing a plurality of N fluid specimens wherein N is an odd number greater than 2;
   b) introducing a first combination of r specimens wherein r is an even number equal to (N+1)/2 into a homogenizing volume to create a homogenized specimen;
   c) introducing at least a portion of the homogenized specimen to the analyzing instrument and recording the results of the analysis maintaining an association with the combination of r specimens;

d) introducing additional different combinations of specimens into said homogenizing volume and repeating steps b) and c); and e) with a programmed digital computer mathematically processing the recorded results to produce analyses corresponding to individual fluid specimens.

2. The method according to claim 1, wherein the fluid specimens are gaseous specimens diluted with a carrier gas.

3. The method according to claim 2, wherein the analyzing instrument is a mass spectrometer.

4. The method according to claim 3, wherein the mathematical processing comprises deconvolution.

5. The method according to claim 4, wherein the mathematical processing comprises a Hadamard transform.

6. The method according to claim 1, wherein each specimen is directed into the homogenizing volume from individual nozzles connected to electronically controlled valves.

7. The method according to claim 6, wherein the nozzle sizes, pressure drops therethrough, and open times of said valves is controlled to introduce a specified mass of each fluid specimen into the homogenizing volume.

8. The method according to claim 7, wherein when the nozzles are not supplying specimen to the homogenizing volume the flow of the specimen is diverted and continued.

* * * * *